(12) United States Patent
Nguyen et al.

(10) Patent No.: US 6,924,102 B2
(45) Date of Patent: Aug. 2, 2005

(54) UTILIZATION OF NUCLEOTIDE PROBES FOR THE MEASUREMENT OF SPECIFIC MRNA FOR THE MOLECULAR DIAGNOSIS OF AUTOSOMAL RECESSIVE SPINAL MUSCULAR ATROPHY

(75) Inventors: Khue Vu Nguyen, San Diego, CA (US); Charles-Michel Wolff, Strasbourg (FR); Philippe Poindron, Plobsheim (FR)

(73) Assignee: Huynh Mai Thi Nguyen, San Jose, CA (US)

(*) Notice: Subject to any disclaimer, the term of this patent is extended or adjusted under 35 U.S.C. 154(b) by 282 days.

(21) Appl. No.: 09/938,013

(22) Filed: Aug. 24, 2001

(65) Prior Publication Data

US 2003/0049627 A1 Mar. 13, 2003

(51) Int. Cl.$^7$ ............... C07H 21/04; C12Q 1/68
(52) U.S. Cl. ............ 435/6; 435/91.1; 435/91.2; 536/23.1; 536/24.3; 536/26.6
(58) Field of Search ............ 435/6, 91.2, 91.1; 536/23.1, 24.3, 26.6

(56) References Cited

U.S. PATENT DOCUMENTS 5,635,351 A * 6/1997 Feuerstein et al.

OTHER PUBLICATIONS

Jong et al. "Analysis of the mRNA transcripts of the SMN gene in the tissue of an SMA fetus and the peripheral blood mononuclear cells of normals, carriers and SMA patients." J. of the Neurological Sciences. vol. 173, pp. 147–153, Feb. 2000.*

Gruber et al. (Histochem Cell Biol. vol. 107, pp. 411–416, 1997).*

Bruce (Am J. Respir. Cell Mol. Biol. vol. 20, pp. 228–236, 1999).*

Van Der Steege et al. "PCR–based DNA test to confirm clinical diagnosis of autosomal recessive spinal muscular atrophy." Lancet. vol. 345, pp. 985–986, Apr. 1995.*

Lefebvre et al. (Genbank Accession No. U438836, May 16, 1996).*

Lefebvre et al. "Identification and Characterization of a spinal muscular atrophy–determining gene." Cell, vol. 80, pp. 155–165, Jan. 13, 1995.*

* cited by examiner

Primary Examiner—Jeanine Goldberg

(57) ABSTRACT

The present invention concerns the development of a quantitative method for the molecular diagnosis of autosomal recessive spinal muscular atrophy (SMA) by measuring the amount of cytosolic mRNA from human muscle cells. Both the procedure using radioactive material and the Enzyme-Linked Immunosorbent Assay (ELISA) nonradioactive method were developed using $^{32}$P-dCTP labeled and biotinylated nucleotide probes. The results obtained demonstrate that the measurement of mRNA could be used as a quantitative method for the molecular diagnosis of SMA. There was a perfect concordance of the results obtained between the procedure using radioactive material, the ELISA method and the single strand conformation polymorphism (SSCP) analysis regarding the negative and positive SMA samples. The methods developed in this study may be applicable to the diagnosis (detection of homozygous and heterozygous deletions in exons 7 and 8 of the SMN gene) and the control of mRNA concentrations in the future gene therapy of patients with SMA.

2 Claims, No Drawings

UTILIZATION OF NUCLEOTIDE PROBES FOR THE MEASUREMENT OF SPECIFIC MRNA FOR THE MOLECULAR DIAGNOSIS OF AUTOSOMAL RECESSIVE SPINAL MUSCULAR ATROPHY

I—FIELD OF THE INVENTION

The present invention concerns the construction of the nucleotide probes (labeling with $^{32}$P-dCTP and with biotin) for the measurement of specific mRNA in view to develop a quantitative method (quantifying by means of BioImager or ELISA with calorimetric detection) for the molecular diagnosis of autosomal recessive spinal muscular atrophy (SMA).

II—BACKGROUND OF THE INVENTION

New gene sequences are discovered daily, and advanced molecular biological techniques are revolutionizing clinical practice in genetic disorders, oncology, infections diseases, etc. . . . Although the current major focus is on using DNA to identify disease genes, mutations, and translocations, or foreign genes as infection agents, the quantification of various specific mRNA molecules in cells and tissues is an attractive field in diagnostic molecular pathology. The concentrations of each specific mRNA are different in normal and disease states and change rapidly in response to various clinical treatments. Among the technologies for assays of mRNA are Northern blotting,[1] RNase protection assay,[2] reverse transcription followed by polymerase chain reaction (RT-PCR),[3,4] in situ hybridization [5] and in situ PCR.[6] Currently, a variety of detection labels can be used, e.g. radioisotopes, fluorescence,[7] and chemiluminescence.[8] Furthermore, once mRNA is reverse-transcribed into cDNA, various gene amplification techniques[9-11] may be applicable. However, because each assay has its own problems, no assay has been accepted as routine for molecular diagnostic purposes; and none of these assays allows researchers to use conventional colorimetric Enzyme-Linked Immunosorbent Assay (ELISA) meters, which are widely available in any laboratory.

To address the above mentioned problem, the important task is to identify a procedure to measure specific mRNA for the molecular diagnosis of genetic disorders. Among a variety of genetics disorders, the spinal muscular atrophy (SMA) is a lethal autosomal recessive disease affecting 1 in 6,000 newborns, and is one of the most common genetic causes of death in childhood.[12-14] SMA is characterised by degeneration of motoneurons from the ventral horns of the spinal cord, leading to symmetrical paralysis of volontary muscles with muscular atrophy. Three different clinical syndromes of SMA (SMA types I, II, and III) can be defined on the basis of age of onset, milestones of development, and age of survival.[15]

All three types of SMA map to chomosome 5q13.3. Recently, Lefebvre et al.[16] identified the SMN gene (Survival Motor Neuron, $T_{BCD541}$) with 8 exons extending over approximately 20 kb. There is a high homologous copy of this gene in the centromeric repeating unit ($C_{BCD541}$); this copy is present in 95.5% of control and hampers detection of absence of the SMN gene. The SMN gene and its centromeric copy differ in their exons by only two base pairs, one in exon 7 and one in exon 8; this difference thus allows the distinction of the SMN gene from its centromeric copy by single-strand conformation polymorphism (SSCP) analysis[16] or by the use of the restriction enzymes.[17] The SMN gene was either absent or interrupted in its exons 7 and 8 in the majority of patients (98%), independent of the type of SMA.[16]

The qualitative techniques for molecular diagnosis of SMA at the DNA level using the SSCP technique[16] and the restriction enzymes[17] have actually become feassible by looking at the presence or absence of exons 7 and 8 of the SMN gene on chromosome 5q13.3. However, these detection methods are hazardous because they use a mutagenic compound (ethidium bromide) for the analysis of the PCR results. In an attempt to overcome this problem, the focus of this research is to develop a quantitative method for the molecular diagnosis of SMA by using the labeled nucleotide probes (labeling with $^{32}$P-dCTP and with biotin) in both the procedure using radioactive material and the Enzyme-Linked Immunosorbent Assay (ELISA) nonradioactive method for the measurement of specific mRNA. Both exons 7 and 8 of the SMN gene are checked for the diagnosis. The sample used for analysis can be either a biological fluid such as whole blood, or a fraction of cells or tissue, in which the RNA can be isolated. In this study, as described herein, are procedures which utilize human muscle cells from muscle biopsies for analysis.

III—PURPOSE OF THE INVENTION

The object of the present invention is to use the nucleotide probes (labeling with $^{32}$P-dCTP and biotin) for the measurement of specific mRNA in view to develop a quantitative method for the molecular diagnosis of SMA. Both the procedure using radioactive material and the Enzyme-Linked Immunosorbent Assay (ELISA) nonradioactive method were developed. Both exons 7 and 8 of the SMN gene were checked for the molecular diagnosis of SMA.

IV—BRIEF DESCRIPTION OF THE INVENTION

The sample used for analysis is either a biological fluid, or a fraction of cells or tissue, in which the RNA can be isolated. In this study, as described herein, are procedures which utilize human muscle cells from muscle biopsies. The methodology generally composes:

1—Growing a cell culture.
2—Isolating and collecting RNA from the cell culture.
3—Subjecting the collected RNA to reverse transcription (RT).
4—Amplifying the RT product to PCR amplification in the presence and absence of digoxigenin-dUTP.
5—Constructing of the nucleotide probes directed at exon 7 or exon 8 of the SMN gene and at HUMEF1AB gene. This gene is used as internal standard for the control of the RT-PCR reactions.
6—Labeling the nucleotide probes with $^{32}$P-dCTP and with biotin.

Use of Radioactive Label for Measurement of mRNA

7—Immobilizing of the PCR products on the nylon membrane
8—Hybridizing the immobilized PCR products with the $^{32}$P-dCTP labeled nucleotide probes.
9—Detecting the hybridized probe by autoradiography and quantifying by means of BioImager Use of Biotin Label in ELISA Procedure for Measurement of mRNA 10—Immobilizing of the streptavidin on the polystyrene microtitration plates
11—Hybridizing the PCR products with the biotin labeled nucleotide probes 12—Immobilizing of the hybridization products on streptavidin coated microtitration plates
13—Adding the peroxidase-conjugated anti-digoxigenin antibodies
14—Adding the peroxidase substrates (chromogene and $H_2O_2$)
15—Adding $H_2SO_4$ to stop the reaction
16—Reading the results (optical density, OD) by means of a microplate reader

V—DETAILED DESCRIPTION OF THE INVENTION

V-I—Materials and Methods

Cell Culture

The methodologies of sample taking (fractions of human muscles from donors suffering from SMA and from corresponding normal controls), culture and maintenance of human muscle cells were established according to the techniques described by Askanas and Engel[18] and Askanas and Gallez-Hawkins[19].

Isolation of RNA

The ribonucleic acid (RNA) was isolated from the cells according to the method described by Sambrook et al.[1] using guanidin/phenol (Tris Reagent™, Euromedex, 67460 Souffelweyersheim, France). The RNA was dissolved in water pre-treated by 0.1% diethyl pyrocarbonate (DEPC, Sigma, St. Louis, Mo.). This RNA solution is ready for subsequent treatment for synthesis of the cDNA. The purity and integrity of the RNA used were analysed by electrophoresis on agarose gel in denaturing conditions.[1]

Reverse Transcription

The synthesis of the cDNA was performed by reverse transcription (RT), described by Sambrook et al.[1] The first copies of cDNA were synthesized using two synthesized oligonucleotides SEQ ID NO:1 and 2 (Genosys biotechnologies, Europe. Ltd., France) with the following sequences: 5'CACATTGCATTTG3' (SEQ ID NO:1) and 5'CTGTCTGTCTCA3' (SEQ ID NO:2). These oligonucleotides SEQ ID NO:1 and 2 were selected by taking the complementary sequence to allow RT. The oligonucleotide SEQ ID NO: 1 was based on the SMN sequence described by Lefebvre et al.[16] between base pairs 1097 and 1 109. The oligonucleotide SEQ ID NO:2 was based on the sequence of the HUMEFIAB gene, encoding for the human elongation factor I-alpha (EFIA), described by Ann et at.[20] between base pairs 881 and 892. This HUMEF1AB gene was used as internal standard for the control of the RT-PCR reactions. The M-MLV Reverse Transcriptase enzyme (Gibco BRL®, Life Technologies Sari, BP 96, 95613 Cergy Pontoise, France) was used for the reverse transcription reaction. This reaction was effected as follows:

To 1.5 µg of total RNA were added 0.3 nmol each of oligonucleotides, 0.6 nmol of 1,4-dithiothreitol threo-1,4-dimercapto-2,3butanediol, DTT (Gibco BRL®), and nucleotides dATP, dCTP, dGTP, dTTP at a concentration of 60 µM. The reaction was conducted in the presence of a reaction buffer for RT of the Gibco BRL® kit and in a total volume of 60 µl. After heating the mixture to 90° C. for 2 minutes and then cooling it on ice for 1 minute, 200 U M-MLV were added; and the mixture was left to 25° C. for 10 minutes and then to 42° C. for 45 minutes.

Amplification

Amplifying the RT products were assessed by using the polymerase chain reaction (PCR) technique.[3,4] Amplification was performed in two different tubes: One for SMN and the other for HUMEF1AB. Four synthesized oligonucleotides SEQ ID NO: 3, 4, 5, 6 (Genosys) were used. They have the following sequences: 5'CCAGGTCTAAAATTCAATGG3' (SEQ ID NO: 3) for the forward primer of SMN, 5'CTGTCTGATCGTTTCTTTAG3' (SEQ ID NO: 4) for the reverse primer of SMN, 5'TGTATTGGATTGCCACACG3' (SEQ ID NO: 5) for the forward primer of HUMEF1AB and 5'CTTCAGCTCAGCAAACTTG3' (SEQ ID NO: 6) for the reverse primer of HUMEF1AB. The oligonucleotides of SEQ ID NO: 3 and SEQ ID NO: 5 (forward primers) were based on the SMN and HUMEF1AB sequences between base pairs 661–680 and 672–690 respectively. The oligonucleotides SEQ ID NO: 4 and SQ ID NO: 6 (reverse primers) were based on the SMN and HUMEF1AB sequences between base pairs 957–976 and 705–723 respectively, in this case however, taking the complementary sequence to allow PCR. Amplification was conducted using a DNA Thermal Cycler (Amplitron® II Thermolyne). The reaction was conducted in a total volume of 75 µl with 2 U of Taq DNA polymerase (Promega Corporation, Madison, Wis., U.S.A.) in the presence of the PCR reaction buffer from Promega kit containing 0.3 nmol each of oligonucleotides, 15 pmol each of nucleotides dATP, dCTP, dGTP, and dTTP, 94 pmol of $MgCl_2$ (Promega) and 15 µl of the reverse transcription reaction medium obtained previously. Amplification conditions were as follows: Denaturation at 94° C. for 1 minute, annealing at 55° C. for 2 minutes, and elongation at 72° C. for 1 minute, each for 25 cycles. The PCR products were analysed, unless otherwise noted, by electrophoresis on a 20 g/l agarose gel to screen for the presence of the appropriate-size band using the fluorescent dye ethidium bromide. Amplifying the RT products by the PCR technique[3,4] was also performed in the presence of 0.75 pmol of digoxigenin-11-dUTP (Boehringer Mannheim, GmbH, Germany). The same conditions for PCR as described previously were used. The PCR products were also analysed by electrophoresis on a 20 g/l agarose gel. The labeling of nucleic acids with digoxigenin was visualized by transfer of the DNA fragments to a nitrocellulose membrane according to the transfer technique described by Southern.[21] The nitrocellulose membrane was then blocked in 30 ml/100 $cm^2$ blocking solution (2% bovine serum albumine, BSA, in phosphate-buffered saline, PBS). After incubation for 1 h at 37° C., the nitrocellulose membrane was washed with PBS and then incubated for 1 h at 37° C. in 30 ml/100 $cm^2$ of blocking solution containing 0.1% Tween® 20 and 3 µl of anti-digoxigenin antibody from sheep, conjugated with alkaline phosphatase (Boehringer Mannheim, GmbH, Germany). Then, the nitrocellulose membrane was washed with PBS and alcaline phosphatase activity was measured in the presence of chemiluminescent substrate: disodium 2-chloro-5-(4-methoxyspiro{1,2-dioxetane-3,2'-(5'-chloro) tricyclo [3.3.1.1.]decan}4-yl)-1-phenyl phosphate (CDP-Star™; Boehringer Mannheim, GmbH, Germany). Reaction conditions for CDP-Star™ were as follows: 100 mM Tris-HCl pH 9.5, 100 mM NaCl, 50 mM $MgCl_2$, 250 nmol/ml CDP-Star™. After incubation for 5 minutes at room temperature, autoradiography was developed using the BIOMAX™MR emulsion film (Eastman Kodak Co. Rochester, N.Y. 14650, U.S.A).

Construction of the Labeled Nucleotide Probes

Both exons 7 and 8 of the SMN gene were checked for the SMA diagnosis. The HUMEF1AB gene was used as internal standard for the control of the RT-PCR reactions.

The RT products were first amplified by the PCR technique performed in the same conditions as described previously using the synthesized oligonucleotides SEQ ID NO: 5 and 6 for HUMEF1AB gene and the synthesized oligonucleotides SEQ ID NO: 4, 7, 8, 9 for SMN gene. They have the following sequences: 5'GTTTCAGACAAAAT-CAAAAAG3' (SEQ ID NO: 7)(forward primer), 5'TCCT-TAATTTAAGGAATGTGA3' (SEQ ID NO: 8)(reverse primer), 5'GAAATGCTGGCATAGAGCAG3' (SEQ ID NO: 9)(forward primer). The oligonucleotides SEQ ID NO: 7 and SEQ ID NO: 9 (forward primers) were based on exons 7 and 8 of the SMN sequences between base pairs 869–889 and 922–941 respectively. The oligonucleotide SEQ ID NO: 8 (reverse primer) was based on exon 7 of the SMN sequence between base pairs 901 and 921, in this case, however, taking the complementary sequence to allow POR. The PCR products were then analysed by ethidium bromide-stained agarose gel, isolated, and purified by phenol-chloroform extraction, dried and resuspended in distilled water according to the method described by Sambrook et al.[1] The purified PCR products so obtained were then polished with Pfu DNA polymerase (Stratagene). The reaction was conducted in the presence of the reagents for PCR polishing of the Stratagene kit and in a total volume of 10 µl containing 2.5 nmol each of nucleotides dATP, dCTP, dGTP, and dTTP, 2.5 U of Pfu polymerase. The reaction conditions (72° C. for 30 min) according to the manufacturer's recommendations were used. The blunt-ended PCR products were then subjected to the ligation reaction into the Bluescript KS(+) plasmid vector predigested by EcoRV (Gibco BRL®). The reaction was conducted in the presence of the reagents for the ligation of the Boehringer Mannheim kit (Rapid DNA ligation kit, Boehringer Mannheim, GmbH, Germany) and in a total volume of 20 µl containing 0.1 µg of digested Bluescript plasmid vector, 1.6 ng of insert DNA, 5 U T4 DNA ligase. The reaction conditions (5 min at room temperature) according to the manufacturer's recommendations were used. After purification by phenol-chloroform extraction, the ligation products were introduced in E. Coli SURE strain by electroporation. The screening for inserts was performed using blue-white color selection. The nucleotide probes so obtained (probes 1, 2 and 3 directed at exons 7 and 8 of the SMN and HUMEF1AB genes respectively) were then labeled with $10^{-3}$ nmol of $\alpha^{32}$P-dCTP (Amersham International) using the previous synthesized oligonucleotides (SEQ ID NO: 4, 7, 8, 9 for the probes 1 and 2 and SEQ ID NO: 5 and 6 for the probe 3) and the reagents (dATP, dGTP, dTTP, Klenow enzyme) of the random primed DNA labeling kit (Boehringer Mannheim, GmbH, Germany). The standard assay conditions of the manufacturer's recommendation of this kit were used. The same conditions of labeling were used for the labeling of these three probes 1, 2 and 3 with biotin-11-dCTP (Sigma, St. Louis, Mo.). The labeling of nucleotide probes with biotin was visualized using the same conditions as that used for visualization of digoxigenin-labeled nucleic acids. Here, 15 µl of anti-biotin-monoclonal antibody conjugated with alkaline phosphatase (Boehringer Mannheim, GmbH, Germany) in 30 ml/100 cm² of blocking solution containing 0.1% Tween® 20 were used.

Use of Radioactive Label for Measurement of mRNA

The total RNA isolated from negative (control) and positive SMA samples (giving a negative and positive results respectively in DNA molecular diagnosis of SMA by means of the SSCP technique) were subjected to RT-PCR (in the absence of digoxigenin-11-dUTP) and analysed by polyacrylamide gel electrophoresis (5% acrylamide, 0.05% bisacrylamide). Following the transfer of the gel to a nylon membrane (Nylon Hybond TM-N, Amersham International), the dotted nucleic acids were UV cross-linked to nylon membrane and hybridized with 30 ml/100 cm² of membrane of hybridization solution (5× standard saline citrate, SSC, 50% formamide, 50× Denhardt) containing 18 µl of $^{32}$P-dCTP labeled nucleotide probe. Hybridization was performed overnight at 42° C. under stirring. After hybridization, the membrane was washed for 10 min at 42° C. in 50 ml/100 cm² of 5×SSC, 10 g/l SDS and for 30 min at 50° C. in 50 ml/cm² of 2×SSC, 10 g/l SDS. This washing was followed by a stringent wash for 30 min at 50° C. in 50 ml/cm² of 0.5×SSC, 10 g/l SDS. The membrane was then directly used for the detection of hybridized probe by autoradiography as described above and quantified by means of Bio-Imager (Fuji).

Use of Biotin Label in ELISA Procedure for Measurement of mRNA

Polystyrene microtitration plates (Maxisorb 96, Immuno Plate, Nunc) were used as the solid phase for the assays. All washes were performed four times with PBS. The substrate solutions for peroxydase, containing 5 mM tetramethyl benzidine (TMB) (Sigma, St. Louis, Mo.) and 25 mM $H_2O_2$, was prepared in citrate phosphate buffer (0.1 M; pH 5.5). After incubation for 15 min at 37° C., the reaction was stopped by the addition of 0.1 ml 0.5 M $H_2SO_4$. The optical density at 450 nm ($OD_{450}$) was measured in a microplate colorimeter (Metertech 960).

For the assay, wells of the microtitration plates were coated with streptavidin (Sigma, St. Louis, Mo.) (1 µg per well) in sodium carbonate buffer (0.1 M; pH 9.6). After incubation overnight at 4° C., the plates were washed, and the uncoated attachment sites on the plates were saturated by incubation for 1 h at 37° C. with a solution of BSA 10 g/l and salmon sperm DNA 100 µg/ml in PBS. The plates were then washed and the coated plates so obtained are ready to use.

For measurement of mRNA, the mRNA isolated from negative (control) and positive SMA samples were first subjected to RT-PCR in the presence of digoxigenin-dUTP as described above. An aliquot of 30 µl of each PCR product was removed and added to a mixture composed of 15 µl of hybridization solution containing salmon sperm DNA 100 µg/ml and 12 µl of biotin labeled nucleotide probe 1, 2, or 3. After denaturation at 97° C. for 10 min, hybridization was performed for 1 h at 42° C. After hybridization, 55 µl of the reaction medium was removed and added to the coated plates. After incubation for 1 h at 37° C., the plates were washed, and 100 µl of a 1-in 1,000 dilution of horseradish peroxidase-labeled sheep antibody anti-digoxigenin (Boehringer Mannheim, GmbH, Germany) in PBS containing 0.05% Tween® 20 was added. After being incubated again for 1 h at 37° C., the plates were washed, and substrate solution was added.

V-II—Results and Discussion

In an attempt to develop a quantitative method for molecular diagnosis of genetic disorders, we have initiated an optimization of the SSCP analysis, a qualitative technique widely used for diagnosis of SMA. In the present study, we use both the procedure using radioactive material and the ELISA nonradioactive method for measuring the amount of cytosolic mRNA from human muscle cells by means of the labeled nucleotide probes.

As shown in Tables 1 and 2, there was a perfect concordance of results obtained between the procedure using radioactive material, the ELISA nonradioactive method and the SSCP analysis regarding the negative an positive SMA samples. All values obtained for the control group were significantly greater than the ones obtained for the SMA positive samples (33 to 76% in radioactive method and 38 to 54% in ELISA method). Despite the small number of samples examined (5 negative and 13 positive SMA samples), the results of this study demonstrate that the measurement of mRNA could be used as a quantitative method for the molecular diagnosis of SMA.

Current techniques are available for the analysis of mRNA, however, because each assay has its own problem, no assay has been accepted as routine for diagnostic purposes. For example, Northern blotting[1] is labor intensive and is not suitable for quantification of mRNA because of uncertainty as to which fraction of applied mRNA is immobilized on the membranes, and most importantly, because some regions of mRNA may be used for immobilization rather than hybridization. RNase protection assay[2] is more sensitive than Northern blotting but usually requires radioactive material and labor-intensive steps, which may not be suitable for assaying large numbers of clinical specimens. PCR[3,4] and other gene amplification procedures may give problems in quantification and reproducibility, although such assays provide the best sensitivity. In situ hybridization[5] and in situ PCR[6] are the only available techniques for localization of gene expression; however each specimen must be examined miscroscopically by expert pathologists with expensive imaging equipment for quantification.

As the result of this study, based on the measurement of specific mRNA, both the procedure using radioactive material and the ELISA nonradioactive method could be applicable to the molecular diagnosis of all genetic disorders associated to a deletion or mutation of gene (s), such as Duchene myopathies, mucoviscidose, or genetic disorders associated to a duplication of the gene such as Charcot-Marie-Tooth disease type 1 A. Here, it is important to note that besides the hazardous problem related to the use of a mutagenic compound (ethidium bromide) for analysis of the PCR results, the qualitative techniques using the SSCP analysis[16] and the restriction enzymes[17] for the molecular diagnosis of SMA at the DNA level do not allow the detection of heterozygous deletion in exons 7 and 8 of the SMN gene (SMA carriers). To overcome this problem, using the mRNA titration curve, our quantitative methods based on the measurement of mRNA may be useful. Moreover, the methods developed in this study may also be useful in the control of mRNA concentrations in medicine and in gene therapy. Indeed, the concentrations of each specific mRNA are different in normal and in disease states and they also change rapidly in response to various clinical treatments.

Concerning the construction of a diagnostic kit, in order to be widely used in clinical laboratories, the diagnostic technique must be safe, easy to handle and automated. For such a purpose, the ELISA method appears to be the best technique because it does not use radioactive material. Furthermore, in comparison to the expensive equipments such as the fluorescent and chemiluminescent plate readers, the colorimetric ELISA meters are less expensive and are widely available in any laboratory. Our ELISA method requires minimal time for setup (only 3 hours to complete the test), and it is easy to interpret the quantitative results obtained. In addition, the precoated plates and the biotinylated nucleotide probes can be prepared in advance and stored without a decrease in reactivity.

VII—REFERENCES

1) Sambrook J, Fritsch E F, Maniatis T. Extraction, purification and analysis of messenger RNA from eukariotic cells. In: Molecular cloning, a laboratory manual, 2nd ed. Cold Spring Harbor, N.Y.: Cold Spring Harbor Laboratory Press, 1989: 7.28–7.52.
2) Petersen N E, Larsen L K, Nissen H, Jensen A, Petersen H et al. Improved RNase protection assay for quantifying LDL receptor mRNA; estimation of analytical imprecision and biological variance in peripheral blood mononuclear cells. *Clin Chem* 1995; 41: 1605–1613.
3) Saiki R K, Scharf S, Faloona F, Mullis K B, Horn C T, Erlich H A, Arnheim N. Enzymatic amplification of β-globine genomic sequences and restriction site analysis for diagnosis of sickle cell anemia. *Science* 1985; 230: 1350–11354.
4) Kawasaki E S, Wang A M. Detection of gene expression. In: PCR technology, Erlich H. A., ed., New York: Stockton, 1989: 89–97.
5) Radnsky R, Bucana C D, Ellis L M, Sanchez R, Cleary K R, Brigati D J, Fidler I J. A rapid colorimetric in situ messenger RNA hybridization technique for analysis of epidermal growth factor receptor in parrafin-embedded surgical specimens of human colon carcinomas. *Cancer Res* 1993; 53: 937–943.
6) Murray G I. In situ PCR. *J Pathol* 1993; 169: 187–188.
7) Fox J L, Hsu P H, Legator M S, Morrison L E, Seelig S A. Fluorescence in situ hybridization: powerful molecular tool for cancer prognosis. *Clin Chem* 1995; 41: 1554–1559.
8) Stanley P E. A survey of more than 90 commercially available luminometers and imaging devices for low-light measurements of chemiluminescence and bioluminescence, including instruments for manual, automatic and specialized operation, for HPLC, LC, GLC and microtitre plates. Part 1: descriptions. *J Biolumin Chemilumin* 1992; 7: 77–108.
9) Van Doornum G J, Buimer M, Prius M, Henquet C J, Coutinho R A, Plier P K et al. Detection of *Chlamydia trachomatis* infection in urine samples from men and women by ligase chain reaction. *J Clin Microbiol* 1995; 33: 2042–2047.
10) Duck P, Alvarado-Urbina G, Burdick B, Collier B. Probe amplifier system based on chimeric cycling oligonucleotides. *Biotechniques* 1990; 9:142–148.
11) Walker G T, Little M C, Nadeau J G, Shank D D. Isothermal in vitro amplification of DNA by a restriction enzyme/DNA polymerase system. *Proc Natl Acad Sci USA* 1992; 86:392–396.
12) Pearn J. The gene frequency of acute Werdning-Hoffmann disease (SMA type I). A total population survey in North East England. *J Med Genet* 1973; 10: 260–265.
13) Pearn J. Incidence, prevalence, and gene frequency studies of chronic childhood spinal muscular atrophy. *J Med Genet* 1978; 15; 409–413.
14) Czeizel A, Hamula J. A Hungarian study on Werdnig-Hoffmann didease. *J Med Genet* 1989; 26: 761–763.
15) Munsat T L, Workshop report. International SMA collaboration. *Neuromusc Disord* 1991; 1: 81.
16) Lefebvre S, Bûrglen L, Reboullet S et al. Indentification and characterization of a spinal muscular atrophy-determining gene. *Cell* 1995; 80: 155–165.
17) Van der Steege G, Grootscholten P M, Van der Vlies et al. PCR-based DNA test to confirm clinical diagnosis of autosomal recessive spinal muscular atrophy. *Lancet* 1995; 345: 985–986.
18) Askanas V, Engel W K. New program for investigating adult human skeletal muscle growth aneurally in tissue culture. *Neurology* 1975; 25: 58–67.
19) Askanas V, Gallez-Hawkins E F. Synergistic influence of polypeptide growth factors on cultured human muscle. *Arch Neurol* 1985; 42: 749–752.
20) Ann D K, Wu M M, Huang T, Carlson D M, Wu R. Retinol-regulated gene expression in human tracheobronchia epithelial cells. Enhanced expression of elongation factor EF-1 alpha. *J Biol Chem* 1988; 263: 3546–3549.
21) Southern EM. Detection of specific sequences among DNA fragments separated by gel electrophoresis. *Mol Biol* 1975; 98: 503–517.

TABLE 1

Comparison of diagnostic methods for SMA

| | SSCP[1] | Our method (radioactive)[3] | | | | | |
|---|---|---|---|---|---|---|---|
| | | Probe 1 (exon 7) | | | Probe 2 (exon 8) | | |
| N* tube | Exons[2] | PSL/mm² | R (%)[4] | Exon 7 | PSL/mm² | R (%)[4] | Exon 8 |
| Control (1) | ndel 7/ndel 8 | 42 | 0 | ndel | 22 | 0 | ndel |
| Control (2) | ndel 7/ndel 8 | 41 | 0 | ndel | 23 | 0 | ndel |
| Control (3) | ndel 7/ndel 8 | 43 | 0 | ndel | 22 | 0 | ndel |
| Control (4) | ndel 7/ndel 8 | 41 | 0 | ndel | 21 | 0 | ndel |
| Control (5) | ndel 7/ndel 8 | 42 | 0 | ndel | 23 | 0 | ndel |
| SMA (6) | del 7/del 8 | 24 | 43 | del | 15 | 32 | del |
| SMA (7) | del 7/del 8 | 14 | 67 | del | 08 | 64 | del |
| SMA (8) | del 7/del 8 | 10 | 76 | del | 07 | 68 | del |
| SMA (9) | del 7/del 8 | 26 | 38 | del | 06 | 73 | del |
| SMA (10) | del 7/del 8 | 09 | 79 | del | 13 | 41 | del |
| SMA (11) | del 7/del 8 | 27 | 36 | del | 12 | 45 | del |
| SMA (12) | del 7/del 8 | 15 | 64 | del | 15 | 32 | del |
| SMA (13) | del 7/del 8 | 13 | 69 | del | 14 | 36 | del |
| SMA (14) | del 7/del 8 | 25 | 40 | del | 11 | 50 | del |
| SMA (15) | del 7/del 8 | 20 | 52 | del | 09 | 59 | del |
| SMA (16) | del 7/del 8 | 19 | 55 | del | 13 | 41 | del |
| SMA (17) | del 7/del 8 | 12 | 71 | del | 14 | 36 | del |
| SMA (18) | del 7/del 8 | 14 | 67 | del | 12 | 45 | del |

[1] single strand conformation polymorphism
[2] del: deleted; ndel: non deleted
[3] The quantification of results obtained is performed by means of Bio-Imager and expressed as PSL/mm²
[4] R: difference = 1 − [(PSL/mm²Control − PSL/mm²SMA)/(PSL/mm²Control)]
The mean value of the control group is used for the calculation of R

TABLE 2

Comparison of diagnostic methods for SMA

| | | Our method (ELISA) | | | | | | | |
|---|---|---|---|---|---|---|---|---|---|
| | | Probe 1 (exon 7) | | | Probe 2 (exon 8) | | | Probe 3 (HUMEF1AB) | |
| N* tube | SSCP[1] Exons[2] | Optical density | R (%)[3] | Exon 7 | Optical density | R (%)[3] | Exon 8 | Optical density | RT-PCR |
| Control (1) | ndel 7/ndel 8 | 0.26 | 0 | ndel | 0.28 | 0 | ndel | 0.55 | positive |
| Control (2) | ndel 7/ndel 8 | 0.28 | 0 | ndel | 0.29 | 0 | ndel | 0.54 | positive |
| Control (3) | ndel 7/ndel 8 | 0.27 | 0 | ndel | 0.26 | 0 | ndel | 0.52 | positive |
| Control (4) | ndel 7/ndel 8 | 0.26 | 0 | ndel | 0.28 | 0 | ndel | 0.51 | positive |
| Control (5) | ndel 7/ndel 8 | 0.27 | 0 | ndel | 0.27 | 0 | ndel | 0.49 | positive |
| SMA (6) | del 7/del 8 | 0.16 | 41 | del | 0.13 | 54 | del | 0.51 | positive |

TABLE 2-continued

Comparison of diagnostic methods for SMA

Our method (ELISA)

| N* tube | SSCP[1] Exons[2] | Probe 1 (exon 7) | | | Probe 2 (exon 8) | | | Probe 3 (HUMEF1AB) | |
|---|---|---|---|---|---|---|---|---|---|
| | | Optical density | R (%)[3] | Exon 7 | Optical density | R (%)[3] | Exon 8 | Optical density | RT-PCR |
| SMA (7) | del 7/ del 8 | 0.16 | 41 | del | 0.16 | 43 | del | 0.48 | positive |
| SMA (8) | del 7/ del 8 | 0.11 | 59 | del | 0.12 | 57 | del | 0.53 | positive |
| SMA (9) | del 7/ del 8 | 0.15 | 44 | del | 0.14 | 50 | del | 0.49 | positive |
| SMA (10) | del 7/ del 8 | 0.19 | 30 | del | 0.16 | 43 | del | 0.5 | positive |
| SMA (11) | del 7/ del 8 | 0.13 | 52 | del | 0.12 | 57 | del | 0.49 | positive |
| SMA (12) | del 7/ del 8 | 0.14 | 48 | del | 0.13 | 54 | del | 0.48 | positive |
| SMA (13) | del 7/ del 8 | 0.17 | 37 | del | 0.14 | 50 | del | 0.55 | positive |
| SMA (14) | del 7/ del 8 | 0.12 | 55 | del | 0.15 | 46 | del | 0.52 | positive |
| SMA (15) | del 7/ del 8 | 0.11 | 59 | del | 0.13 | 54 | del | 0.5 | positive |
| SMA (16) | del 7/ del 8 | 0.13 | 52 | del | 0.15 | 46 | del | 0.51 | positive |
| SMA (17) | del 7/ del 8 | 0.15 | 44 | del | 0.12 | 57 | del | 0.49 | positive |
| SMA (18) | del 7/ del 8 | 0.16 | 41 | del | 0.16 | 43 | del | 0.5 | positive |

[1] single strand conformation polymorphism
[2] del: deleted; ndel: non deleted
[3] R: difference = $1 - [(OD_{450}Control - OD_{450}SMA/OD_{450}Control)]$
The mean value of the control group is used for the calculation of R

We claim:

1. A quantitative method for molecular diagnosis of spinal muscular atrophy (SMA) comprising:
    obtaining a sample from a human suspected of having SMA containing mRNA of survival motor neuron (SMN-mRNA) and the mRNA of human elongation factor 1-alpha (HUMEF1AB-mRNA)
    reverse transcribing the mRNA using primers consisting of SEQ ID NO:1 for the synthesis of cDNA from SMN-mRNA giving SMN-cDNA and consisting of SEQ ID NO:2 for the synthesis of cDNA from HUMEF1AB-mRNA giving HUMEF1AB-cDNA;
    amplifying the SMN-cDNA by PCR using primers consisting of SEQ ID NO:3 and SEQ ID NO:4 and the HUMEF1AB-cDNA by PCR using primers consisting of SEQ ID NO:5 and SEQ ID NO:6
    immobilizing of the PCR products on a nylon membrane
    hybridizing the immobilized PCR products with radioactive $^{32}$p-dCTP labeled nucleotide probes wherein the probes are generated by PCR amplification of nucleic acids consisting of SEQ ID NO:7 and 8 for exon 7; nucleic acids consisting of SEQ ID NO:9 and SEQ ID NO:4 for exon 8 and, nucleic acids consisting of SEQ ID NO:5 and SEQ ID NO:6 for HUMEF1AB,
    measuring SMN-mRNA by means of BioImager device using the radioactive $^{32}$p-dCTP labeled nucleotide probes by detecting the hybridized probes using autoradiography and quantifying the amount of SMN-mRNA by means of a BioImager device
    wherein the quantification of between 9 and 27 PSL/mm2 for exon 7 and between 6 and 15 PSL/mm2 for exon 8 is indicative of SMA disease.

2. A quantitative method for molecular diagnosis of spinal muscular atrophy (SMA) comprising:

obtaining a sample from a human suspected of having SMA containing mRNA of survival motor neuron (SMN-mRNA) and the mRNA of human elongation factor 1-alpha (HUMEF1AB-mRNA)

reverse transcribing the mRNA using primers consisting of SEQ ID NO:1 for the synthesis of cDNA from SMN-mRNA giving SMN-cDNA and consisting of SEQ ID NO:2 for the synthesis of cDNA from HUMEF1AB-mRNA giving HUMEF1AB-cDNA amplifying the SMN-cDNA by PCR using primers consisting of SEQ ID NO:3 and SEQ ID NO:4 and the HUMEF1AB-cDNA by PCR using primers consisting of SEQ ID NO:5 and SEQ ID NO:6 in the presence of digoxigenin-11-dUTP hybridizing the obtained PCR products with the biotin-11-dCTP labeled nucleotide probes wherein the probes are generated by PCR amplification of nucleic acids consisting of SEQ ID NO:7 and 8 for exon 7; nucleic acids consisting of SEQ ID NO:9 and SEQ ID NO:4 for exon 8 and, nucleic acids consisting of SEQ ID NO:5 and SEQ ID NO:6 for HUMEF1AB, immobilizing the hybridized products on streptavidin coated polystyrene microtitration plates adding the peroxidase-conjugated anti-digoxigenin antibodies adding the peroxidase substrates consisting of $H_2O_2$ and chromogene (tetramethyl benzidine)

adding $H_2SO_4$ to stop the reaction measuring SMN-mRNA by means of microplate reader in an ELISA procedure using the biotin-11-dCTP labeled nucleotide probes immobilized on streptavidin polystyrene microtitration plates by detecting the hybridized probes using ELISA and quantifying the amount of SMN-mRNA by determining the optical density (OD)

wherein an OD of between 0.11 and 0.19 for exon 7 and an OD of between 0.12 and 0.16 for exon 8 is indicative of SMA disease.

\* \* \* \* \*

SEQUENCE LISTING

<160> NUMBER OF SEQ ID NOS: 9

<210> SEQ ID NO 1
<211> LENGTH: 13
<212> TYPE: DNA
<213> ORGANISM: Homo sapiens

<400> SEQUENCE: 1
cacattgcat ttg                                               13

<210> SEQ ID NO 2
<211> LENGTH: 12
<212> TYPE: DNA
<213> ORGANISM: Homo sapiens

<400> SEQUENCE: 2
ctgtctgtct ca                                                12

<210> SEQ ID NO 3
<211> LENGTH: 20
<212> TYPE: DNA
<213> ORGANISM: Homo sapiens

<400> SEQUENCE: 3
ccaggtctaa aattcaatgg                                        20

```
<210> SEQ ID NO 4
<211> LENGTH: 20
<212> TYPE: DNA
<213> ORGANISM: Homo sapiens

<400> SEQUENCE: 4
ctgtctgatc gtttctttag                                              20

<210> SEQ ID NO 5
<211> LENGTH: 19
<212> TYPE: DNA
<213> ORGANISM: Homo sapiens

<400> SEQUENCE: 5
tgtattggat tgccacacg                                               19

<210> SEQ ID NO 6
<211> LENGTH: 19
<212> TYPE: DNA
<213> ORGANISM: Homo sapiens

<400> SEQUENCE: 6
cttcagctca gcaaacttg                                               19

<210> SEQ ID NO 7
<211> LENGTH: 21
<212> TYPE: DNA
<213> ORGANISM: Homo sapiens

<400> SEQUENCE: 7
gtttcagaca aaatcaaaaa g                                            21

<210> SEQ ID NO 8
<211> LENGTH: 21
<212> TYPE: DNA
<213> ORGANISM: Homo sapiens

<400> SEQUENCE: 8
tccttaattt aaggaatgtg a                                            21

<210> SEQ ID NO 9
<211> LENGTH: 20
<212> TYPE: DNA
<213> ORGANISM: Homo sapiens

<400> SEQUENCE: 9
gaaatgctgg catagagcag                                              20
```